United States Patent
Farley et al.

(10) Patent No.: US 8,852,282 B2
(45) Date of Patent: Oct. 7, 2014

(54) METHODS AND SYSTEMS FOR INTERBODY IMPLANT AND BONE GRAFT DELIVERY

(76) Inventors: Daniel K. Farley, Traverse City, MI (US); Christopher T. Martin, Empire, MI (US); Stephanie Zalucha, Williamsburg, MI (US); Miguelangelo J. Perez-Cruet, Bloomfield Hills, MI (US)

( * ) Notice: Subject to any disclaimer, the term of this patent is extended or adjusted under 35 U.S.C. 154(b) by 0 days.

(21) Appl. No.: 13/614,471

(22) Filed: Sep. 13, 2012

(65) Prior Publication Data
US 2013/0006366 A1 Jan. 3, 2013

Related U.S. Application Data

(63) Continuation-in-part of application No. 13/219,288, filed on Aug. 26, 2011, now abandoned.

(60) Provisional application No. 61/377,691, filed on Aug. 27, 2010.

(51) Int. Cl.
 A61F 2/44 (2006.01)
 A61F 2/30 (2006.01)
 A61F 2/46 (2006.01)

(52) U.S. Cl.
 CPC ..... *A61F 2/4611* (2013.01); *A61F 2310/00359* (2013.01); *A61F 2002/30266* (2013.01); *A61F 2002/30843* (2013.01); *A61F 2310/00017* (2013.01); *A61F 2002/30281* (2013.01); *A61F 2310/00407* (2013.01); *A61F 2002/30892* (2013.01); *A61F 2002/30616* (2013.01); *A61F 2002/30736* (2013.01); *A61F 2002/30828* (2013.01); *A61F 2310/00958* (2013.01); *A61F 2/447* (2013.01); *A61F 2002/4627* (2013.01); *A61F 2002/3008* (2013.01); *A61F 2310/00161* (2013.01); *A61F 2002/3083* (2013.01); *A61F 2310/000223* (2013.01); *A61F 2002/4628* (2013.01); *A61F 2002/305* (2013.01)
 USPC ............... 623/17.16; 623/17.11; 606/249

(58) Field of Classification Search
 USPC ............. 606/246, 248, 249; 623/17.11–17.16
 See application file for complete search history.

(56) References Cited

U.S. PATENT DOCUMENTS 4,874,368 A 10/1989 Miller
(Continued)

FOREIGN PATENT DOCUMENTS

WO WO2005/016783 A1 2/2005
WO WO2005/060367 A2 7/2005

OTHER PUBLICATIONS

Patent Cooperation Treaty, Notification of Transmittal of the International Search Report and the Written Opinion of the International Searching Authority, or the Declaration, in International Application No. PCT/US11/49377, dated Dec. 23, 2011 (12 pages).

(Continued)

*Primary Examiner* — Pedro Philogene
*Assistant Examiner* — Christina Negrellirodrigue
(74) *Attorney, Agent, or Firm* — McAndrews, Held & Malloy, Ltd.

(57) ABSTRACT

A spacer for implantation between adjacent vertebrae is provided. The spacer includes a distal end and a proximal end. The spacer also includes top and bottom surfaces spaced by sides. The top and bottom surface define a height, and the sides define a width. Each of the sides of the spacer may include a depressed region sunk into the side including a sloped surface at least toward the proximal end of the spacer. The distance between the sloped surfaces of the sides may decrease proximally to form a web having a leading edge proximate to the proximal end of the spacer. The web may be sized and configured to aid distribution of bone graft material to either side of the spacer, wherein bone graft material is supplied to a site of interest is distributed to at least one side of the spacer.

20 Claims, 10 Drawing Sheets

(56) References Cited

U.S. PATENT DOCUMENTS

| | | | |
|---|---|---|---|
| 6,616,593 | B1 | 9/2003 | Elliott |
| 6,620,185 | B1 | 9/2003 | Harvie |
| 2002/0160032 | A1 | 10/2002 | Long |
| 2003/0014116 | A1 | 1/2003 | Ralph |
| 2003/0236573 | A1* | 12/2003 | Evans et al. ............... 623/23.58 |
| 2006/0085008 | A1 | 4/2006 | Jaggi |
| 2007/0282441 | A1* | 12/2007 | Stream et al. ............. 623/17.11 |
| 2008/0154377 | A1 | 6/2008 | Voellmicke |
| 2008/0172128 | A1* | 7/2008 | Perez-Cruet et al. ...... 623/17.16 |
| 2008/0260598 | A1* | 10/2008 | Gross et al. ................... 422/162 |
| 2009/0137946 | A1 | 5/2009 | Nassiri |
| 2012/0277754 | A1 | 11/2012 | Lin et al. |

OTHER PUBLICATIONS

Patent Cooperation Treaty, Notification of Transmittal of the International Search Report and the Written Opinion of the International Searching Authority, or the Declaration, in International Application No. PCT/US11/49371, dated Jan. 19, 2012 (13 pages).

PCT International Preliminary Report on Patentability, in International Application No. PCT/US11/49371, Oct. 11, 2012 (55 pages).

PCT, Notification of Transmittal of International Preliminary Report on Patentability, in International Application No. PCT/US11/49371, Jan. 24, 2013 (65 pages).

European Patent Office, Communication pursuant to Rules 70(2) and 70a(2) EPC, in Application No. 11820735.6, dated Feb. 7, 2014.

European Patent Office, Communication with extended European search report, in Application No. 11820735.6, dated Jan. 21, 2014.

* cited by examiner

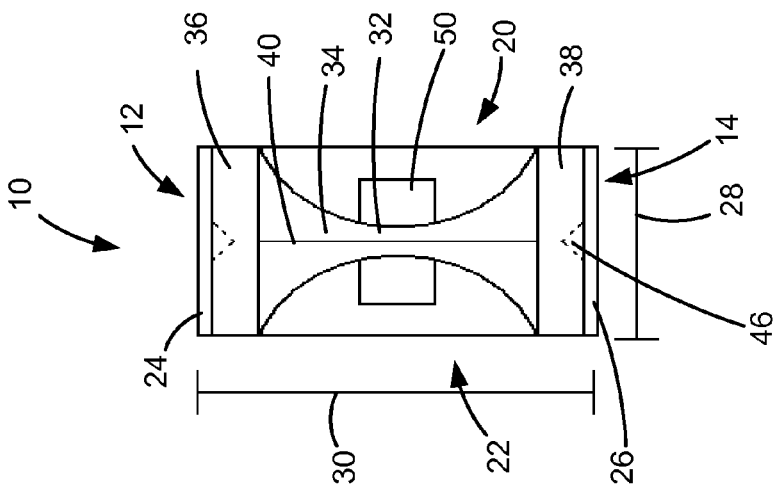
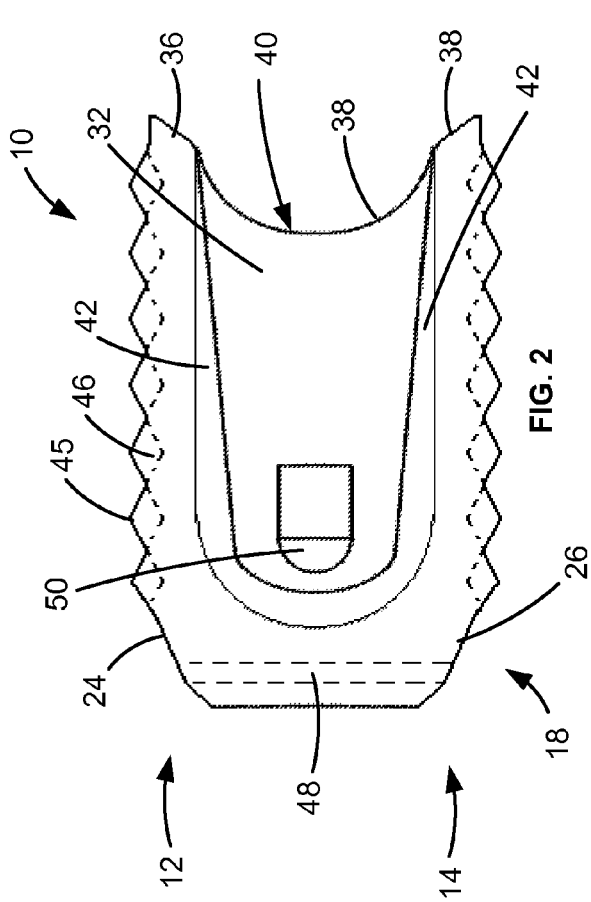
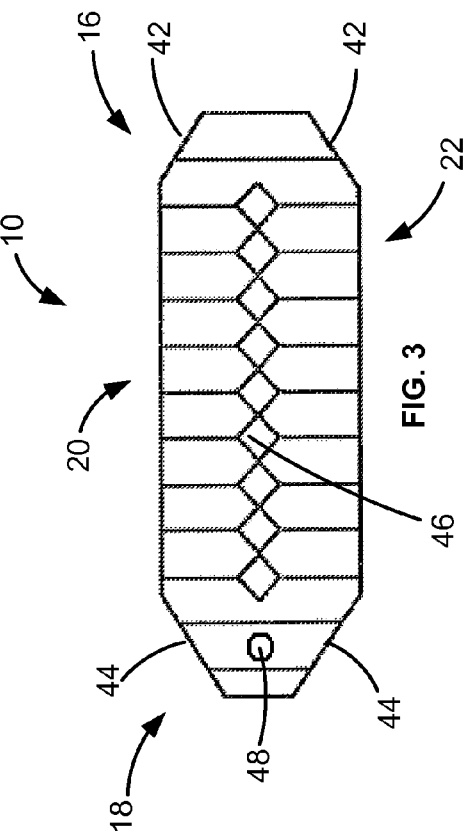
FIG. 4
FIG. 2
FIG. 3

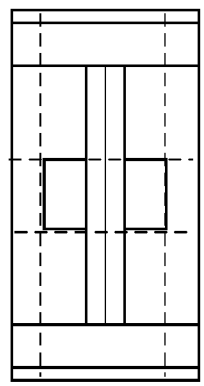
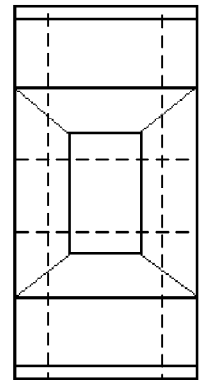
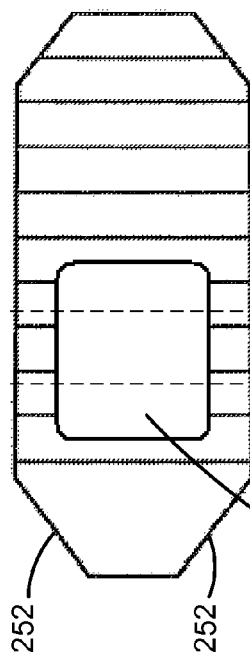
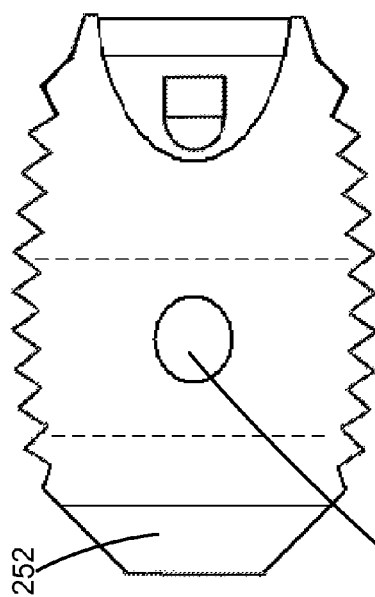

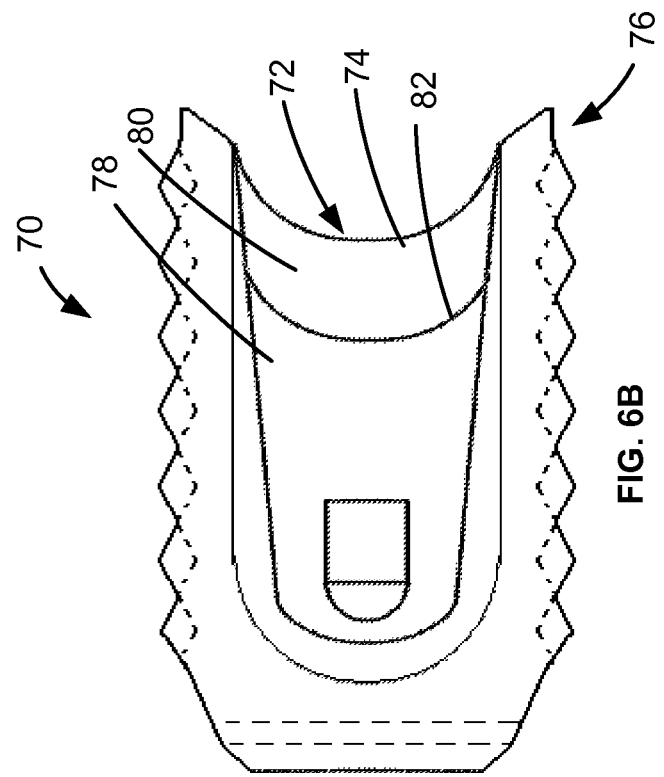
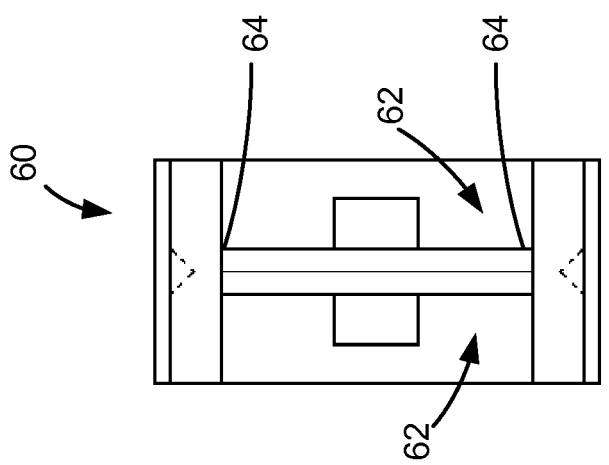
FIG. 6B
FIG. 6A

METHODS AND SYSTEMS FOR INTERBODY IMPLANT AND BONE GRAFT DELIVERY

CROSS-REFERENCE TO RELATED APPLICATION

This application is a continuation-in-part, and claims priority to, U.S. patent application Ser. No. 13/219,288, filed Aug. 26, 2011, which claims priority to U.S. Patent Application No. 61/377,691, filed Aug. 27, 2010. The entire contents of these two applications are hereby incorporated by reference in their entireties.

BACKGROUND OF THE INVENTION

The present invention relates to systems and methods for providing spinal implants, for example, to be used in connection with spinal fusion.

Spinal fusion is a surgical procedure that fuses two or more vertebrae together using bone graft materials supplemented with devices. Spinal fusion may be performed for the treatment of chronic neck and/or back pain, trauma, and neoplasms. Spinal fusion can be used to stabilize and eliminate motion of vertebrae segments that may be unstable, or move in an abnormal way, that can lead to discomfort and pain. Spinal fusion may be performed to treat injuries to the vertebrae, degeneration of spinal discs, abnormal spinal curvature, and/or a weak or unstable spine.

Spinal fusion generally requires a graft material, usually bone material, to fuse the vertebrae together. The bone graft material can be placed over the spine to fuse adjacent vertebrae together. Alternatively, a device (i.e. cage) may be positioned between the vertebrae being fused and filled with the bone graft material. Such a cage can include holes that allow the vertebrae and the graft material to grow together to provide fusion, with the cage supporting the weight of the vertebrae while the fusion is occurring. Most of these cages are limited to only a few cubic centimeters of bone graft material thus limiting the fusion area achieved. Because the fusion mass is under pressure, fusion can be promoted. The disc space height can be restored, taking pressure off of the nerves. The spine alignment, foraminal height, and canal diameter can be restored. In some cases the graft can be placed with minimal disruption of muscles and ligaments using minimally invasive approaches to the spine, thus preserving the normal anatomical integrity of the spine. Other interbody device assemblies are also presently known. These include those disclosed in U.S. patent application Ser. No. 11/623,356, filed Jan. 16, 2007, titled "Minimally Invasive Interbody Device," and Ser. No. 11/932,175, filed Oct. 31, 2007, titled "Minimally Invasive Interbody Device Assembly," which are hereby incorporated by reference in their entirety.

Typically, the bone graft material is autogenous bone material taken from the patient, or allograft bone material harvested from a cadaver. Synthetic bone material can also be used as the graft material. Generally, the patient's own bone material offers the best fusion material since it offers osteoinductive, osteoconductive, and osteogenesis properties. Known bone fusion materials include iliac crest harvest from the patient, bone graft extenders, such as hydroxyapatite and demineralized bone matrix, and bone morphogenic protein.

Minimally invasive surgical procedures have been devised in an attempt to preserve normal anatomical structures during spinal surgery. Many known procedures for spinal fusion, however, still are more invasive than desired. Additionally, many known procedures do not provide the level of control over the delivery and placement of the bone graft material as could be desired. Additionally, current interbody devices only allow for a limited application of bone material (i.e., cages), and because of their relative size place the neural elements at risk during placement, often resulting in undersized implants being placed.

It is therefore one object of the present invention to provide a spinal implant system that reduces approach related morbidity, allows for more bone graft placement and/or provides improved control of the delivery and/or placement of bone graft material.

BRIEF SUMMARY OF THE INVENTION

These and other objects of the invention are achieved, in certain embodiments, in a spacer for implantation between adjacent vertebrae. The spacer includes a distal end and a proximal end. The spacer also includes top and bottom surfaces spaced by sides. The top and bottom surfaces define a height, and the sides define a width. In certain embodiments, the height is greater than the width, wherein the spacer may be inserted with its sides oriented toward surfaces of adjacent vertebrae and then rotated into place with the top and bottom surface oriented toward the surfaces of the adjacent vertebrae to maintain a desired space between the adjacent vertebrae. In such an application of the device, nerve root retraction can be reduced and improved disc height restoration achieved. The sides of the spacer may include depressed regions sunk into the side (for example a cutouts) that define a web which may include one or more surfaces, for example surfaces that slope, at least toward the proximal end of the spacer. In one example, the distance between the surfaces of the web may decrease proximally to form a wedge having a leading edge proximate to the proximal end of the spacer. The surface(s) may be sized and configured to aid distribution or disbursement of bone graft material to either side of the spacer, wherein bone graft material may be supplied to a site of interest and distributed to at least one side of the spacer. Thus, the interbody device may be placed, in certain embodiments rotated to restore disc height, and bone then passed on either side of the implant allowing for better and more bone graft delivery into the disc interspace.

In certain embodiments, the depressed regions sunk into the sides may comprise cutouts that form a web separating top and bottom caps at least at the proximal end of the spacer. The web may include one or more surfaces, for example surfaces that slope, at least toward the proximal end of the spacer. In some embodiments, the thickness of the web may decrease proximally to form a wedge having a leading edge proximate to the proximal end of the spacer. Further, in some embodiments, the top and bottom caps may include surfaces that taper such that the top cap and bottom cap become narrower toward the proximal end of the spacer. In certain embodiments, the web includes a tip that defines a generally sharp point.

The depressed regions (for example, cutouts) may define a web that may include first and second surfaces. In some embodiments, the first and second surfaces may have a slope, perhaps different slopes wherein one of the surfaces slopes inward proximally more sharply than the other. In certain embodiments, at least one side of the web may include a mounting feature configured to help secure the spacer with at least one of an inserter and a funnel. For example, in certain embodiments the mounting feature includes a button extending from a surface of the web.

Certain embodiments of the present invention provide a spinal implant system for positioning and fixing an implant between adjacent vertebrae that includes a spacer, a feed reservoir, and a plunger. The spacer includes a distal end and a proximal end. The spacer also includes top and bottom surfaces spaced by sides. The top and bottom surfaces define a height, and the sides define a width. In certain embodiments, the height is greater than the width, wherein the spacer may be inserted with its sides oriented toward surfaces of adjacent vertebrae and then rotated into place with the top and bottom surface oriented toward the surfaces of the adjacent vertebrae to maintain a desired space between the adjacent vertebrae. The sides of the spacer may include depressed regions sunk into the side (for example a cutouts) that define a web which may include one or more surfaces, for example surfaces that slope, at least toward the proximal end of the spacer. In one example, the distance between the surfaces of the sides decreases proximally to form a wedge having a leading edge proximate to the proximal end of the spacer. The surfaces(s) may be sized and configured to aid distribution of bone graft material to either side of the spacer, wherein bone graft material may be supplied to a site of interest and distributed to at least one side of the spacer. The feed reservoir defines a passageway through which bone graft material may be delivered to the spacer when the spacer is positioned as desired between adjacent vertebrae. The feed reservoir includes an alignment feature configured to align the feed reservoir with the spacer so that bone graft material delivered to the spacer through the feed reservoir is distributed or dispersed to at least one side of the spacer. The plunger is configured to be accepted by the passageway of the feed reservoir, and is configured to help advance bone graft material along a length of the feed reservoir.

In certain embodiments, the depressed regions form a web separating top and bottom caps at least at the proximal end of the spacer. The web may include one or more surfaces, for example surfaces that slope, at least toward the proximal end of the spacer. In some embodiments, the thickness of the web, at least over a portion of the web, may decrease proximally to form the wedge. Further, the alignment feature of the feed reservoir may include a notch sized to be accepted by the web. In certain embodiments, the top cap and bottom cap include surfaces that taper, such that the top and bottom cap become narrower toward the proximal end of the spacer. Further, the alignment feature of the feed reservoir may include a notch cut through top and bottom walls of the feed reservoir, with the notch sized and configured to accept a portion of the top cap and bottom cap of the spacer.

In certain embodiments, the feed reservoir is asymmetric about a vertical plane through the center of the spacer when the feed reservoir is aligned with the spacer.

In still other embodiments, the system also includes an inserter. The inserter includes the feed reservoir and a gripping portion. The gripping portion is configured to grasp the spacer during insertion and positioning of the spacer. The gripping portion in certain embodiments includes a load bearing portion sized to contact vertebrae during rotation of the spacer. Additionally or alternatively, the gripping portion may include a graft opening sized and configured to allow bone graft material to be distributed to at least one side of the spacer when the spacer is positioned in the gripping portion.

In certain embodiments, the feed reservoir includes a first portion and a second portion separated by a wall, while the plunger includes a first plunger and second plunger. The first plunger is accepted by the first portion of the feed reservoir, and the second plunger is accepted by the second portion of the feed reservoir. Thus, bone graft material can be advanced down the portions of the feed reservoir either independently or simultaneously. Further, the plunger may include a handle, with the first and second plungers removably joined to the handle.

Certain embodiments of the present invention provide a method for maintaining adjacent vertebrae in a desired position. The method includes providing a spacer. The spacer includes a distal and proximal end, and top and bottom surfaces spaced by sides. Each of the sides of the spacer may include depressed regions sunk into the sides (for example cutouts) that define a web which may include one or more surfaces, for example surfaces that slope, at least toward the proximal end of the spacer. In one example, the distance between the surfaces of the sides decreases proximally to form a wedge having a leading edge proximate to the proximal end of the spacer. The surface(s) may be sized and configured to aid distribution of bone graft material to either side of the spacer. In certain embodiments, the method also includes positioning the spacer between the adjacent vertebrae with the sides oriented toward surface of adjacent vertebrae, and then rotating the spacer so that the top and bottom surfaces of the spacer are oriented toward the surfaces of the adjacent vertebrae to maintain a desired space between the adjacent vertebrae. The method further includes positioning a feed reservoir so that a passageway of the feed reservoir is proximate to the web of the spacer. Further, the method includes introducing bone graft material through the feed reservoir to a site of interest proximate to the spacer, wherein the bone graft material is directed by the web to be distributed to a site proximate to at least one side of the spacer.

BRIEF DESCRIPTION OF THE SEVERAL VIEWS OF THE DRAWINGS

FIG. 2 illustrates a side view of the spacer of FIG. 1.

FIG. 3 illustrates a top view of the spacer of FIG. 1.

FIG. 4 illustrates an end view (looking from the proximal end) of the spacer of FIG. 1.

FIG. 5A illustrates a top view of a spacer, formed in accordance with an embodiment of the present invention.

FIG. 5B illustrates a side view of the spacer of FIG. 5A.

FIG. 5C illustrates an end view (looking from the proximal end) of the spacer of FIG. 5A.

FIG. 5D illustrates an end view (looking form the distal end) of the spacer of FIG. 5A.

FIG. 6A illustrates an end view of a spacer formed in accordance with an embodiment of the present invention viewed from the proximal end.

FIG. 6B illustrates a side view of a spacer formed in accordance with an embodiment of the present invention.

DETAILED DESCRIPTION

Figure 1:
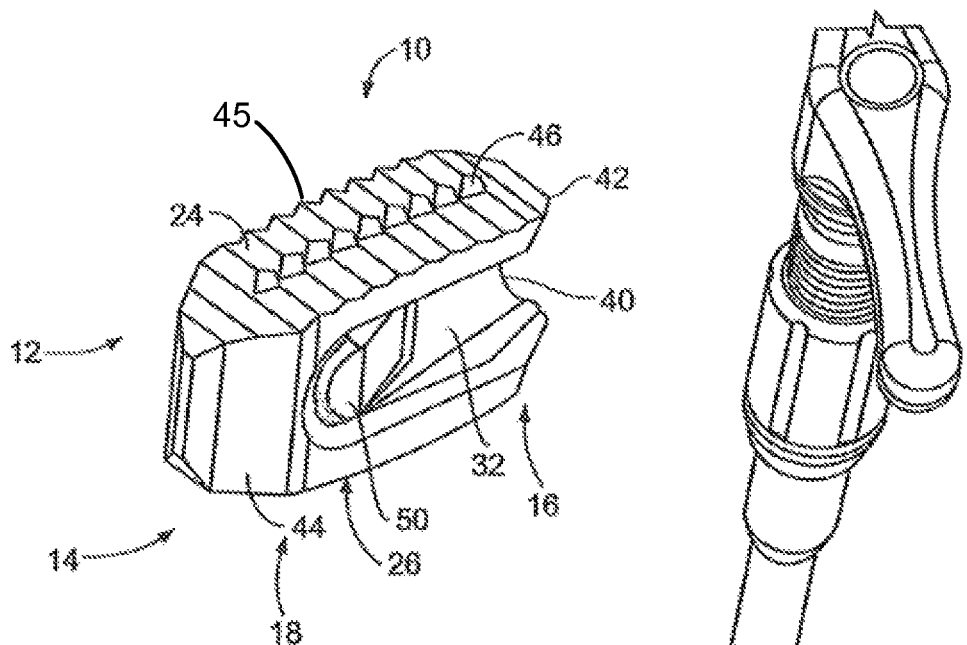
FIG. 1 illustrates a perspective view of a spinal implant, or spacer, formed in accordance with an embodiment of the present invention.

FIG. 1 illustrates a perspective view of a spinal implant, or spacer, 10; FIG. 2 illustrates a side view of the spacer 10; FIG. 3 illustrates a top view of the spacer 10; and FIG. 4 provides an end view (looking from the proximal end) of the spacer 10. The spacer 10 is sized and adapted to maintain a desired spatial relationship between adjacent vertebrae. Different sizes of spacers are used to accommodate different procedures and/or sizes of patient anatomy. The spacer 10 may, for example, be made of PEEK (polyether ether ketone), titanium, carbon fiber, bone allograft, or a plurality of materials. The spacer 10 may, for example, be solid in certain embodiments, and, in other embodiments, include a hollow portion or portions. The spacer 10 includes a top side 12 and a bottom side 14. (The spacer 10 illustrated in FIGS. 1-4 is symmetric, so "top" and "bottom" sides may be interchangeable). Alternatively, the spacer can be of greater height distally to allow for lordotic disc height restoration. The spacer 10 also includes a proximal end 16 and a distal end 18. The proximal end 16 is the end of the spacer 10 designed to be located closer to a practitioner during a procedure, and the distal end 18 is the end of the spacer 10 designed to be oriented more deeply inside a patient during a procedure. The spacer 10 also includes sides 20, 22. The top side 12 includes a top surface 24 and the bottom side 14 includes a bottom surface 26. The spacer 10 defines a width 28 that is substantially less than its height 30 (with the height being defined by the distance between the top surface 24 and bottom surface 26, and the width defined by the distance between the sides 20, 22). A cutout 32 is cut into each side proximate to the proximal end 16. Cutouts are an example of a depressed region sunk into the surface of the sides. The cutouts may be formed by removing material from the sides, but may be formed in alternate fashion as well, such as, for example, a molding process. In the illustrated embodiment, the cutout 32 includes a semi-circular edge proximate to its proximal end. In alternate embodiments, the shape of the cutout may be different at its proximal end. For example, the proximal end of the cutout may define a substantially vertical line.

As best seen in FIGS. 2 and 4, the cutouts 32 help define a web 34, a top cap 36, and bottom cap 38. The top cap 36 and bottom cap 38 help form part of the top side 12 and bottom side 14, respectively. In the illustrated embodiment, the cutouts 32 are rounded as seen from the proximal end 16. In alternate embodiments, the cutouts 32 may define a plurality of different shapes, such as, for example, generally perpendicular (see also FIG. 6A). The web 34 may include one or more surfaces, for example two surfaces located on opposite sides of the web. The surfaces of the web 34 may act to help distribute or disperse bone graft material to either side of the spacer 10 as bone graft material is supplied to the site of interest. In some embodiments, the depth of the cutouts 32 into the sides 20, 22 increases proximally along at least a portion of the length of the cutout. Put another way, the web 34 may include one or more surfaces that slope inward (toward each other) proximally so that the distance between the sloped surfaces decreases proximally. In certain embodiments, the depth of the cutouts 32 may increase along the length of the entire cutout. In certain other embodiments, the depth may be constant for a portion of the cutout resulting in a generally flat surface having zero slope (and generally constant thickness of the web along that portion of the cutout), and then slope inwardly toward the proximal end at an intermediate point along the length of the cutout. In still other embodiments, multiple sloped surfaces having different slopes may be formed.

Thus, in some embodiments, the thickness of the web 34 (or the distance between the surfaces of the web) may decrease proximally along at least a length of the web 34 In these embodiments, the web 34 may be seen as forming a wedge 40, with the sharper portion of the wedge 40 oriented proximally. The tip of the wedge may, for example, define a generally sharp point. In other embodiments, the tip of the wedge may be blunt, rounded, or define a narrow flat surface. The wedge 40 may act to help distribute or disperse bone graft material to either side of the spacer 10 as bone graft material is supplied to the site of interest. In the illustrated embodiment, the web 34 and caps 36, 38 define generally distinct shapes toward the proximal end 16, but the cutout does not extend through the distal end 18, and the distal end 18 is a generally solid mass.

In certain embodiments, such as the embodiments depicted in FIGS. 5A-5D, the spacer may not be a generally solid mass. For example, in certain embodiments, a spacer 250 may include provisions for allowing bone graft material into and/or through additional portions of the spacer. For example, in certain embodiments, one or more holes 260 extending through the spacer between and through the top and bottom surfaces, and/or one or more holes 262 extending through the spacer between and through the sides, may be located, for example, distal of the cutouts, to provide for the inclusion of bone graft material through the spacer in communication with vertebral surfaces. The dotted lines shown in FIGS. 5A-5D may help to show that holes 260, 262 may extend through the body of the spacer, for example with two holes extending in perpendicular directions and perhaps intersecting.

The caps 36, 38 may also define surfaces 42 that taper in width to become narrower toward the proximal end 16 of the spacer 10, as seen in FIGS. 2 and 3 for example. In certain alternate embodiments, the cutout may run along the height of the spacer, thereby forming a continuous inwardly sloping surface, instead of defining generally distinct caps and a web.

Referring to FIG. 2, in the illustrated embodiment, the web 34 has a circular or crescent-shaped profile when viewed from the sides. In alternate embodiments, other configurations or shapes may be employed. For example, the profile could appear as a series of line segments instead of a continuous curve. As another example, the web 34, when viewed from the side as in FIG. 2, may define a generally vertical line extending from at or near the proximal edge of the top cap 36 to the bottom cap 38. Such a web may be advantageous with generally smaller spacers that use feed reservoirs having smaller cross-sectional areas. In still other embodiments, the web may have a similar vertical shape at its edge, but the edge of the web may be offset from the proximal edge of the spacer. Thus, the web need not be precisely at the proximal edge of the spacer, but may, for example, be located appropriately at other locations proximate to the proximal end of the spacer.

Figure 1A:
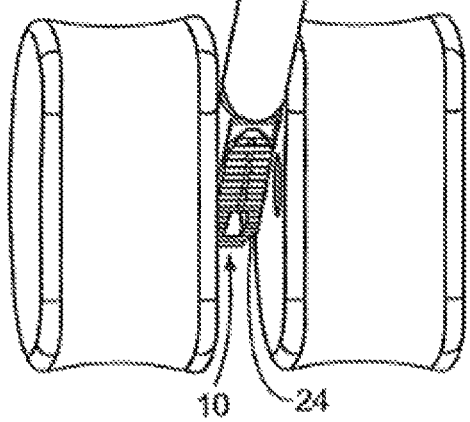
FIG. 1A illustrates a perspective view of a spinal implant being inserted between two vertebrae in a horizontal orientation.
Figure 1B:
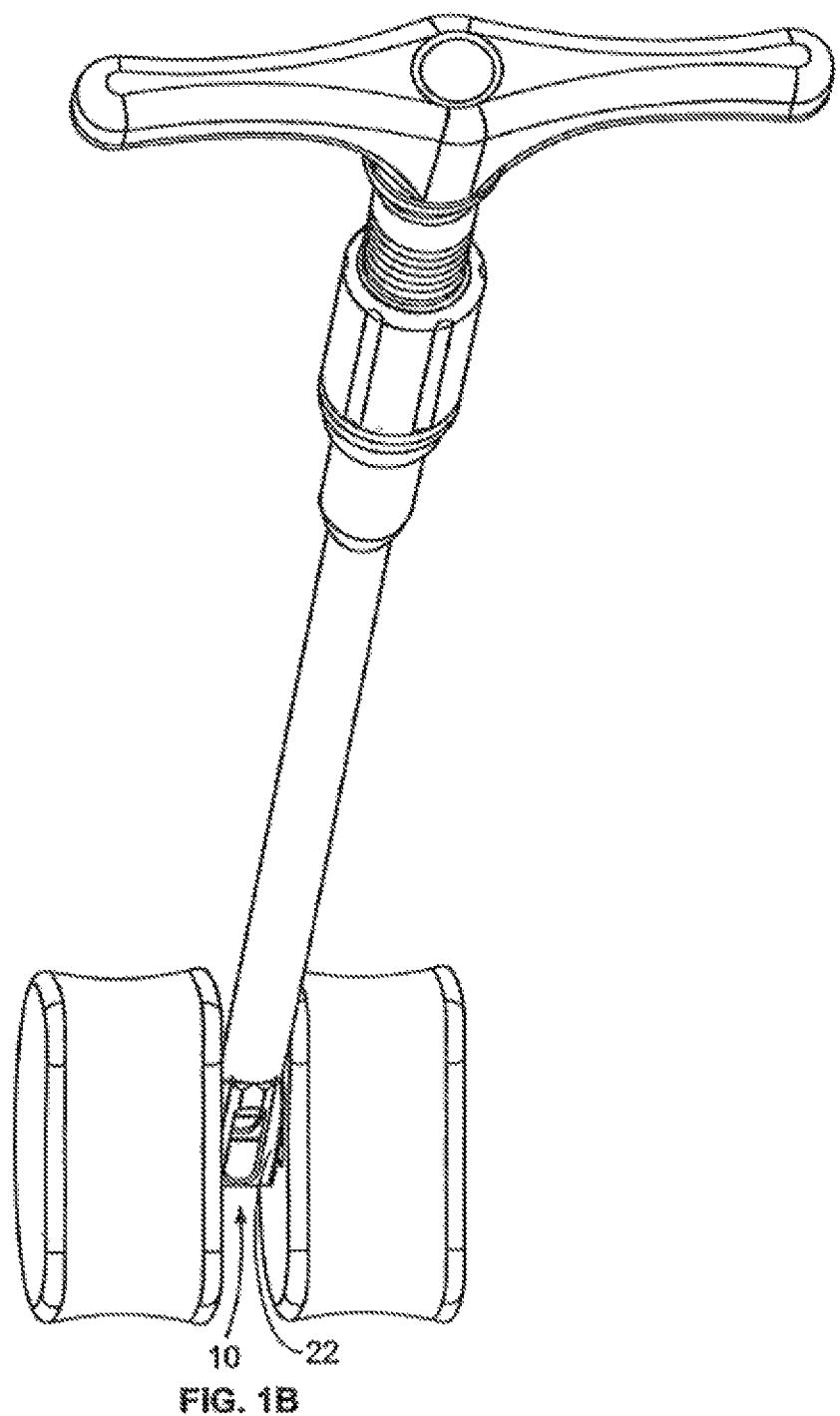
FIG. 1B illustrates a perspective view of a spinal implant rotated to its vertical position between two vertebrae.

FIG. 1A illustrates a perspective view of a spacer being inserted in a first orientation between two vertebrae, and FIG. 1B illustrates the spacer between the two vertebrae after being rotated to a second orientation to distract the vertebrae. The height 30 of the spacer 10 is selected to provide support between adjacent vertebrae. To place the spacer 10 in a patient, the spacer 10 is first inserted with its height oriented horizontally between the desired vertebrae, as shown in FIG. 1A (put another way, an axis defined by a line drawn perpendicularly through the top and bottom surfaces 24, 26 is generally perpendicular to the spine). Oriented thus, in what is referred to herein as the horizontal orientation, the spacer 10 may be inserted between the vertebrae with clearance between the spacer and the vertebrae. Then, once in place between the desired vertebrae, the spacer 10 is rotated so that its top surface 24 abuts against the bottom of the higher of the vertebrae to be fixed, and its bottom surface 26 abuts against the top of the lower of the vertebrae to be fixed, and the vertebrae are distracted, as shown in FIG. 1B. In this position, referred to herein as the vertical orientation, the spacer 10 has a sufficient height and rigidity to position and/or support the vertebrae in a desired spatial relationship to each other. For example, a spacer with height of about 11 millimeters and a width of about 7 millimeters may be placed between vertebrae spaced about 7 millimeters apart, and then rotated to its vertical position to space the vertebrae about 11 millimeters apart, thereby providing about 4 millimeters of distraction.

Regarding spacers, the top and bottom surfaces (for example surfaces 24, 26) may be straight or they may be curved so that a height across a central portion of the surfaces is greater than a height across an end portion of the surfaces. The top and bottom surfaces of the spacer illustrated in FIGS. 1-4 are substantially straight with no curve or a slight curve. The spacers 250, 11 illustrated in FIGS. 5B and 6A may be of a style that has curved top and bottom surfaces. The dimensions of the curve of the top and bottom surfaces may be selected to correspond to the shape of the vertebral surfaces to be engaged.

Referring to FIGS. 1-4, the surfaces 24, 26 may include ridges (for example, ridges 45) to help secure the spacer 10 in place between vertebrae. Surfaces 24, 26 may also include features (for example, features 46) to help secure the spacer 10 in place between vertebrae. Ridges may take the form of accordion-style peaks and valleys, although other embodiments may include other styles and shapes of raised and lowered sections to enhance grip. The features may take the form of a series of crevasses into the surfaces 24, 26. In the illustrated embodiment, the features 46 include a number of uniform pyramid-shaped crevasses arranged in a line along a central portion of surface 24 extending from distal end 18 to proximal end 16. In alternate embodiments, such pyramid-shaped crevasses may form a grid or array, or other features such as ridges, or other shapes of crevasses and or other materials may be used.

The illustrated spacer 10 also includes a radio-opaque marker 48 located proximal to the distal end 18. This marker can extend on the distal end 18 from top 24 to bottom 26. Alternative, the marker can extend from one side 20 to side 22. Additional radio-opaque markers can be placed on the proximal portion 16 of the spacer 10. These markers can be made from a plurality of radio-opaque materials. The marker(s) 48 is designed to allow the use of fluoroscopy to confirm the positioning of the spacer 10 during a procedure.

The sides 20, 22 of the spacer 10 illustrated in FIGS. 1-4 also include tapered surfaces 44 proximal to the distal end 18 (also seen in surfaces 252 of FIGS. 5A and 5B). These tapered surfaces, for example surfaces 44, form a leading edge, or bullet nose, to help ease insertion of the spacer 10 into an incision in the disc space and between vertebrae. For example, when the spacer 10 is introduced between vertebrae in its horizontal orientation, the leading portion formed by the tapered surfaces 44 provides a smaller cross-section to be inserted between the vertebrae.

The spacer 10 may also include additional features to help secure and/or align the spacer 10 with, for example, an inserter used to position the spacer and/or a funnel used to provide bone graft material to desired locations around the spacer 10. In the illustrated embodiment, the spacer 10 includes mounting buttons 50 extending from a portion of the cutout of each side for attaching an inserter to the spacer 10. The buttons 50 are sized and positioned to accept slots of the inserter, as also discussed below. In alternate embodiments, a spacer may include, for example, holes sunk into each side, with the holes being sized and positioned to accept pins protruding from a surface of the inserter, or a plurality of shapes to hold the spacer 10 during insertion.

In certain embodiments, a spacer is positioned using an inserter. Once positioned, the spacer is released by the inserter, which is then removed. A feed reservoir, such as a funnel, is then introduced to provide bone graft material to the site of interest around the spacer. In other embodiments, the feed reservoir may be incorporated in the inserter. In certain embodiments, a funnel may be aligned and/or secured to a spacer by mating one or more features on the funnel (such as a hole or slot, for example) to one or more of features of the spacer that were also used to secure the inserter to the spacer (such as a pin or button, for example). As may be further appreciated in connection with the below discussion of funnels, in alternate embodiments, the spacer may include a separate feature to help align the funnel. For example, a portion of the web of the spacer may be accepted by a v-shaped notch in the funnel. In certain embodiments, the caps may be aligned with an opening in the funnel. As an example of an additional alternative, one or more of the caps may include an alignment feature, such as a tab or wedge, that corresponds to a corresponding alignment feature, such as a slot or a notch, on the funnel. In certain embodiments, the funnel and inserter are made of stainless steel, which allows them to be sterilized and re-used.

FIG. 6A illustrates an end view of a spacer 60 formed in accordance with an embodiment of the present invention, as viewed from the proximal end. The spacer 60 may be similar in many respects to the spacer 10 illustrated in FIGS. 1-4, for example the spacer may include cutouts 62 that form a web. The cutouts 62 of spacer 60 may differ, however, in that they may not have the rounded, or scooped, profile of cutouts 32 of spacer 10. As shown in FIG. 6A, the cutouts 62 have generally perpendicular corners 64. The web formed by cutouts 62 may include one or more surfaces, for example two surfaces located on opposite sides of the web. The surfaces of the web may act to help distribute or disperse bone graft material to either side of the spacer 60 as bone graft material is supplied to the site of interest. Similar to the spacer of FIGS. 1-4, the depth of the cutouts 62 into the sides may increase proximally along at least a portion of the length of the cutout. Put another way, the web may include one or more surfaces that slope inward (toward each other) proximally so that the distance between the sloped surfaces decreases proximally. Thus, the web of the spacer 60 may also be seen as forming a wedge, with the sharper portion of the wedge oriented proximally. Numerous alternative cutout shapes (and by association, web shape shapes and surface shapes) are possible. For example, the slope of the surfaces of the web as it progresses proximally may be linear, curved, or stepped. Further, a series of cutouts may be employed, or the area of the side that is cut into may vary. Further, when viewing the spacer 60 toward the proximal end, the surfaces/cutouts may be substantially straight (from top to bottom), or they may be channeled (for example, like the rounded or scooped style depicted in the spacer of FIGS. 1-4).

Surfaces formed by cutouts (for example, the cutouts 62 of spacer 60 or the cutouts 32 of spacer 10) may be made of the same material as the rest of the spacer, or they may be made of a different material. For example, the surfaces may be made of PEEK (polyether ether ketone), titanium, carbon fiber, bone allograft, or a plurality of materials. Surfaces may be solid in certain embodiments, and, in other embodiments, may include a hollow or perforated portion or portions.

FIG. 6B illustrates a side view of a spacer 70 formed in accordance with an embodiment of the present invention. The spacer 70 may be similar in many respects to the spacers 10 and 60 previously discussed. As seen in the side view illustrated in FIG. 6B, the web 72 of the spacer 70 includes a circular cutout 74 proximate to the proximal end 76. Each side/surface of the web 72 of spacer 70 defines a first sub-surface 78 and a second sub-surface 80. The second sub-surface 80, as seen from the side, is defined by a curved edge 82, which locates the transition from the first sub-surface 78 to the second sub-surface 80. The sub-surfaces 78, 80 may have a slope, for example the sub-surfaces may slope inward toward each other moving proximally. The inward slope of the second sub-surface 80 as it progresses proximally may be greater than the inward slope of the first sub-surface 78. Thus, the web 72 of the spacer 70 may define two differently sloped sub-surfaces as it progresses toward the proximal edge of the web.

Figure 7:
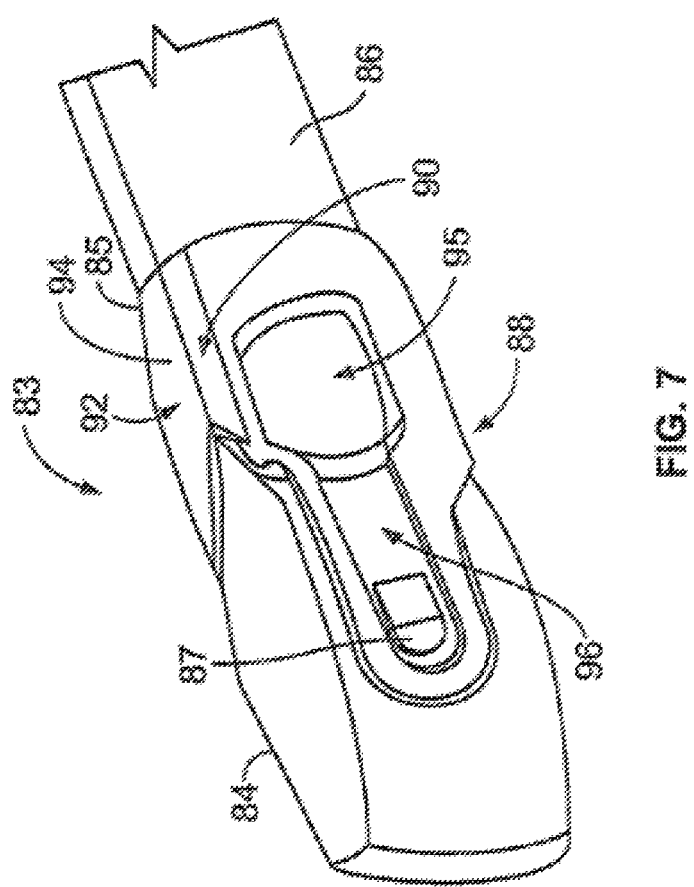
FIG. 7 illustrates a perspective view of an implant system including an inserter joined to a spacer formed in accordance with an embodiment of the present invention.

As can be seen in FIGS. 5-7, spacers may include a body that is shaped differently than the spacers depicted and described in relation to FIGS. 1-4. For example, referring to FIG. 5B, the spacer 250 may have curved top 254 and bottom 256 and the top and bottom may include more prominent ridges. In another example, referring to FIG. 7, the proximal end of the spacer when viewed from the top may substantially form a point, and the sides of the spacer may be curved smoothly instead of the angular sides depicted in FIGS. 1-4. It should be understood, however, that the descriptions provided herein of implant systems, inserters and the like may apply to many varieties of shapes of spacers, including the spacer shapes of FIGS. 1-7, and other shapes, for example as shown in other figures such as FIG. 8.

FIG. 7 illustrates a side view of a spacer 84 formed in accordance with an embodiment of the present invention. FIG. 7 also illustrates a perspective view of an implant system 83 including an inserter 85 joined to a spacer 84. The inserter 85 includes a shaft 86 and a gripping portion 88. The gripping portion 88 is adapted to grasp and release the spacer 84. The gripping portion 88 includes a first half 90 and a second half 92, which are capable of being biased by a grasping mechanism of the shaft 86. For example, the shaft 86 may include a tapered portion associated with threads on the inside of the shaft that may be turned one way to tighten the gripping portion 88 (that is, bring the two halves together) and turned in the opposite direction to loosen the gripping portion 88 (that is, allow the two halves to move apart from each other).

In the illustrated embodiment, the gripping portion 88 is sized so that it may include a load bearing portion 94 that defines a cross-sectional area corresponding to the cross-sectional area of the spacer 84, such that the load bearing portion 94 contacts the vertebrae during the rotation of the inserter 85 and spacer 84 and thereby takes some of the load encountered as the assembly contacts the vertebrae and distracts the vertebrae. In other embodiments, the gripping portion 88 may define a smaller volume such that it does not contact the vertebrae or take any load during the rotation process.

Each half of the gripping portion 88 of the illustrated inserter 85 includes a feature or features for gripping the spacer 84. In the illustrated embodiment, the spacer 84 includes buttons 87 on each side. For example, a button may extend from a surface of a cutout, or for example the first sub-surface 78. Each opening 93 of the gripping portion 88 includes a graft opening 95 and a slot 96. The slot 96 is sized to cooperate with a feature of the spacer 84 (for example, button 87) to allow the spacer 84 to align with and be retained by the inserter 85. Alternatively, the button 87 can be absent and the slot 96 eliminated to create a solid device holder. The graft opening 95 is sized to allow bone graft material to be supplied via the inside of the shaft 86, to be distributed to either side of the spacer 84, and then to pass through the graft opening 95. As bone graft material accumulates along the sides of the spacer 84 and the gripping portion 88 of the inserter 85, the accumulating bone graft material may make removal of the inserter 85 more difficult. Further, removal of the inserter 85 after bone material has been added may result in the disturbance and/or removal of bone graft material from its desired delivery location. Thus, in certain alternate embodiments, the inserter is disengaged from the spacer before bone graft material is supplied. In such embodiments, the shaft may be solid, and/or the graft opening may be smaller or not present.

As mentioned above, in certain embodiments, the inserter may be removed before addition of bone graft material. In certain embodiments where the inserter is removed before the addition of bone graft material, or where additional bone graft material is desired to be added after the removal of the inserter, a funnel may be used to supply bone graft material to the site of interest around the spacer. Funnels provided by various embodiments of the present invention may provide a variety of shapes, including, for example, circular, oval, or otherwise round, or a polygon shape such as square or rectangular, as well as symmetric or asymmetric. Further, funnels of certain embodiments may have generally constant cross-sectional shapes and areas, or may have different cross-sectional shapes and/or areas at various points along their length. In certain embodiments, a plunger is provided to help push bone graft material through the funnel to the site of interest. The plunger is sized and adapted to be received by the interior of the funnel with a slight clearance to allow the plunger to be moved along the length of the funnel.

Figure 8:
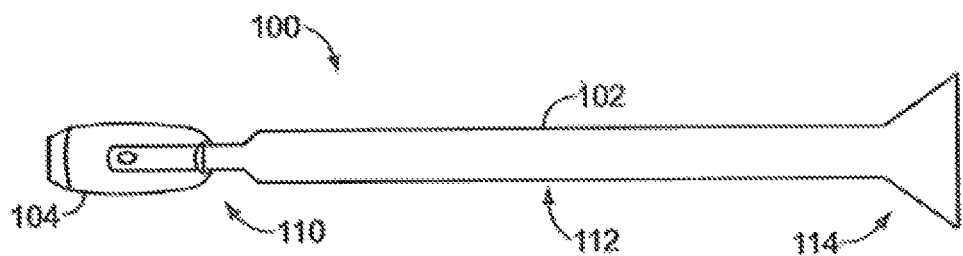
FIG. 8 illustrates a side view of an implant system including a funnel formed in accordance with an embodiment of the present invention.
Figure 9:
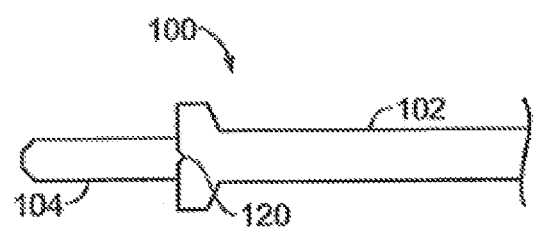
FIG. 9 illustrates a top view of the implant system of FIG. 8.

FIG. 8 illustrates a side view of a spinal implant system 100 including a funnel 102 and a spacer 104 formed in accordance with an embodiment of the present invention, and FIG. 9 illustrates a top view of the system 100. In FIGS. 8-9, the funnel 102 is shown positioned to deliver bone graft material to the spacer 104. In certain embodiments, the overall length of the funnel 102 is about 8 inches. The spacer 104 may be similar in many respects to the spacers discussed above. The funnel 102 includes a distal portion 110, an intermediate portion 112, and a proximal portion 114. The distal portion 110 includes a notch 120 sized and configured to cooperate with the leading edge of the web of the spacer 104 to align the funnel 102 and spacer 104 during delivery of bone graft material. In alternate embodiments, the distal portion may be adapted to cooperate with one or more caps and/or one or more features located on a cap or caps of a spacer to position and align the funnel. In further alternate embodiments, the distal portion of the funnel may be adapted to cooperate with features located on the web as well as the caps of the spacer, or with features located on a body of a spacer.

In the illustrated embodiment, the intermediate portion 112 is a generally circular tube, sized to provide a desired amount of bone graft material to a site of interest. For example, in certain embodiments, the intermediate portion 112 may have an outside diameter of approximately 9 millimeters. The proximal portion 114 is enlarged to provide for easier addition of bone graft material. The distal portion 110 of the illustrated funnel 102 has a substantially oval cross section, with a reduced height and increased width relative to the spacer 104, allowing for more efficient distribution of bone graft material to the sides of the spacer 104. In alternate embodiments, for example, a funnel may have a substantially oval shaped cross section along its entire length. Such a cross-section may be generally equally sized along the length of the funnel, or may, for example, expand to a greater cross-sectional area toward the distal end of the funnel. In certain embodiments, the transition from the smaller cross section to the larger is as short as practicably feasible. Further, in certain embodiments, the funnel includes vents to ease movement of the plunger.

Figure 10:
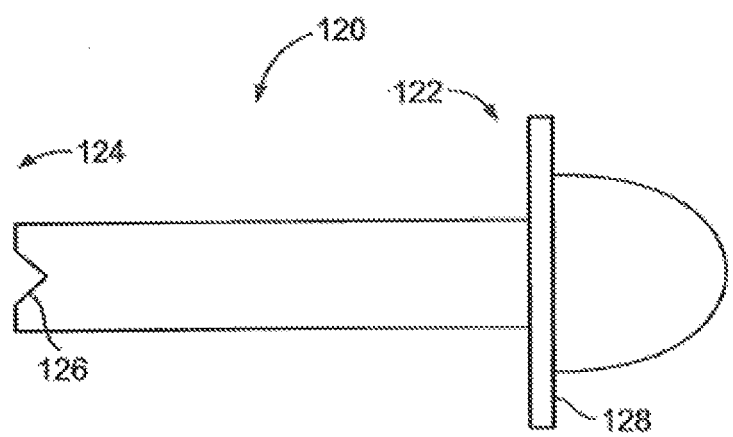
FIG. 10 illustrates a top view of a plunger formed in accordance with an embodiment of the present invention.

FIG. 10 provides a top view of a plunger 120 formed in accordance with an embodiment of the present invention. The plunger 120 illustrated in FIG. 10 is designed to work with a funnel having a generally oval cross-section, and to advance bone graft material distally through the funnel. A variety of sizes of funnel and plunger may be provided to accommodate a variety of sizes required for various patients and procedures. For example, in certain embodiments, generally oval plungers for use with oval funnels may be sized in a range from about 3 millimeters to about 17 millimeters in width and from about 5 millimeters to about 20 millimeters in height. In alternate embodiments, the plunger may take different shapes. For example, a substantially circular plunger could be used with a funnel that is substantially circular along most of its length, and a substantially rectangular plunger could be used with a funnel that is substantially rectangular along its length. The plunger 120 includes a proximal end 122 and a distal end 124, and a notch 126 located proximate to the distal end 124. The notch 126 is sized to cooperate with a corresponding feature on a spacer (similar to the above discussion regarding the funnel). In alternate embodiments, the plunger may not include such a notch. Additionally, the plunger (and/or funnel the plunger is designed to cooperate with) may include a stop or other features designed to prevent the plunger from being inserted too deeply into the funnel. For example, the plunger could include a handle 128 or tab (not shown) at its proximal end extending out from the body of the plunger to prevent the proximal end of the plunger from extending past a selected point such as the proximal end of the funnel.

Figure 11:
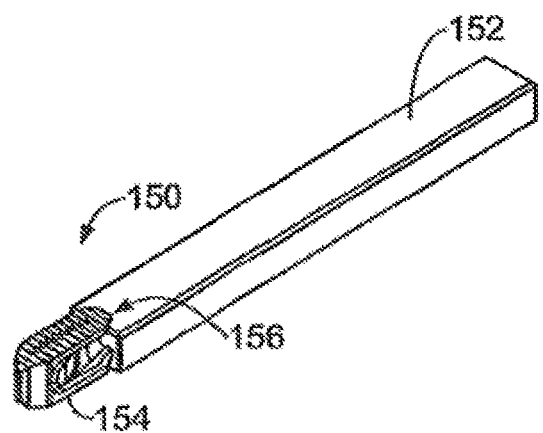
FIG. 11 illustrates a perspective view of an implant system including a rectangular, symmetric funnel formed in accordance with an embodiment of the present invention.
Figure 12:
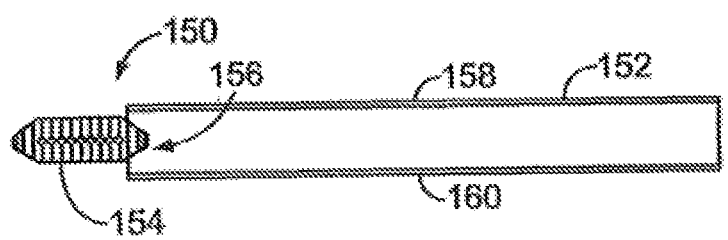
FIG. 12 illustrates a top view of the implant system of FIG. 11.

FIG. 11 illustrates a perspective view of a spinal implant system 150 including a funnel 152 and a spacer 154, and FIG. 12 illustrates a top view of the spinal implant system 150. As can best be seen in FIG. 12, the funnel 152 is symmetric about a vertical plane through the center of the spacer 154 when the spacer 154 and funnel 152 are positioned in place during a procedure to provide bone graft material to a site of interest. The funnel 152 illustrated in FIGS. 11 and 12 is generally rectangular and is wider than it is high, allowing for greater distribution of bone graft material around the sides of the spacer 154 than to the top or bottom of the spacer 154. For example, in certain embodiments, the funnel is formed from a rectangular tube having a height of about 7 millimeters, a width of about 11 millimeters, and a wall thickness of about 0.5 millimeters. In other embodiments, different sizes and shapes, such as generally circular or oval funnels, may be used. The illustrated funnel 152 includes an alignment feature 156 configured to cooperate with a feature of the spacer 154 to help properly align the funnel 152 with the spacer 154 during delivery of bone graft material. For example, in the illustrated embodiment, the alignment feature 156 comprises a notch cut through both the top and bottom walls of the funnel 152 that accepts a portion of the caps of the spacer 154. In alternate embodiments, an alignment feature may be configured to accept the web of a spacer, the web and the caps of a spacer, or a different portion of a spacer. The width of the funnel 152 is such that its sides 158, 160 are located laterally far enough away from the alignment feature to allow bone graft material to flow to both sides of the spacer 152.

Figure 13:
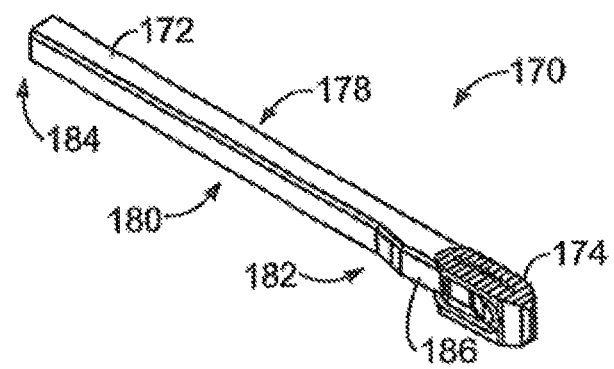
FIG. 13 illustrates a perspective view of an implant system including a rectangular, asymmetric funnel formed in accordance with an embodiment of the present invention.
Figure 14:
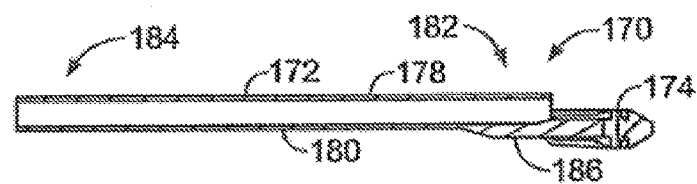
FIG. 14 illustrates a top view of the implant system of FIG. 13.

FIG. 13 illustrates a perspective view of a spinal implant system 170 including a funnel 172 and a spacer 174, and FIG. 14 illustrates a top sectional view of the spinal implant system 170. The funnel 172 includes a distal end 182 and a proximal end 184. As can best be seen in FIG. 14, the funnel 172 is asymmetric about a vertical plane through the center of the spacer 174 when the spacer 174 and funnel 172 are positioned in place during a procedure to provide bone graft material to a site of interest. The funnel 172 illustrated in FIGS. 12 and 14 is generally square shaped along most of its length, with an offset 186 toward its distal end 182. For example, the funnel 172 may generally include a generally square length of tubing with an additional amount of solid material added to form the offset 186. The two pieces may, for example, be soldered together and then heat treated to make the funnel 172. In certain embodiments, the tubing portion of the funnel 172 may be about 5.5 millimeters by 5.5 millimeters with a wall thickness of 0.5 millimeters. The illustrated funnel 172 is configured to cooperate with the web of the spacer 174 to align the funnel 172 and spacer 154. In alternate embodiments, an alignment feature may be configured to accept the caps of a spacer, the web and the caps of a spacer, or a different portion of a spacer. For instance, a funnel otherwise generally similar to funnel 172 may be configured to cooperate with features on the cap of a spacer to align the spacer and funnel. For example, in certain embodiments, a funnel designed to engage the cap of a spacer similarly sized to spacer 174 may have a height of about 7.0 millimeters, a width of about 5.50 millimeters, and a wall thickness of 0.5 millimeters along most of its length. The illustrated funnel 172 includes an alignment feature 176 configured to cooperate with a feature of the spacer 174 to help properly align the funnel 172 with the spacer 174 during delivery of bone graft material. For example, in the illustrated embodiment, the alignment feature 176 comprises a notch cut through of the height of the funnel 172 and through a portion of the offset 186 that accepts the leading edge of the web of the spacer 174. Thus, the alignment feature 176 is off-center of the funnel, allowing first side 178 of the funnel to protrude laterally further away from the center of the spacer 154 than second side 180 protrudes. The width of the funnel 172 is such that first side 178 is located laterally far enough away from the corresponding side of the spacer to allow bone graft material to flow to its side of the spacer 174, but second side 180 is located laterally closer to the alignment feature such that either a smaller amount of bone graft material, or no bone graft material, is allowed to flow to its side of the spacer 174. To use such an asymmetric funnel, the funnel would first be positioned to provide bone graft material to one side of the spacer. Once a sufficient amount of bone graft material was provided to one side of the spacer, the funnel would be removed, rotated 180 degrees, and re-positioned to provide bone graft material to the other side of the spacer. Use of such an asymmetric funnel allows for a smaller overall cross-sectional area of the funnel, thereby aiding to make the required procedure less invasive. Further, use of such an asymmetric funnel makes it easier to provide different quantities of bone graft material to different sides of a spacer.

Figure 15:
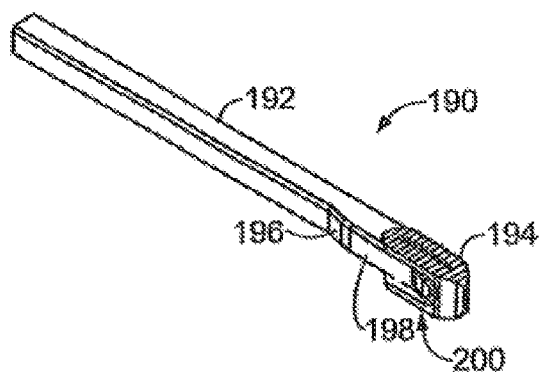
FIG. 15 illustrates a perspective view of an implant system including a funnel formed in accordance with an embodiment of the present invention.

FIG. 15 illustrates a perspective view of a spinal implant system 190 including a funnel 192 and a spacer 194. The funnel 192 may be generally similar to funnel 172, discussed above, in many respects. However, funnel 192 further includes an arm 198 extending from an offset 196. Toward the distal end of the arm 198, the arm 198 includes a securement feature 200 configured to cooperate with a feature of the spacer 194 to more securely connect the funnel 192 to the spacer 194. For example, the securement feature 200 may comprise a pin adapted to be accepted by a hole in the spacer 194. Other arrangements are possible. For example, the securement feature 200 may be a slot similar to the above describe slot of an inserter that accepts a button of the spacer. As a further example, the securement feature may be a sloped or otherwise shaped surface that corresponds to a portion of the surface of the cutout of the spacer that is accepted by the cutout in a generally snug fit.

Figure 16:
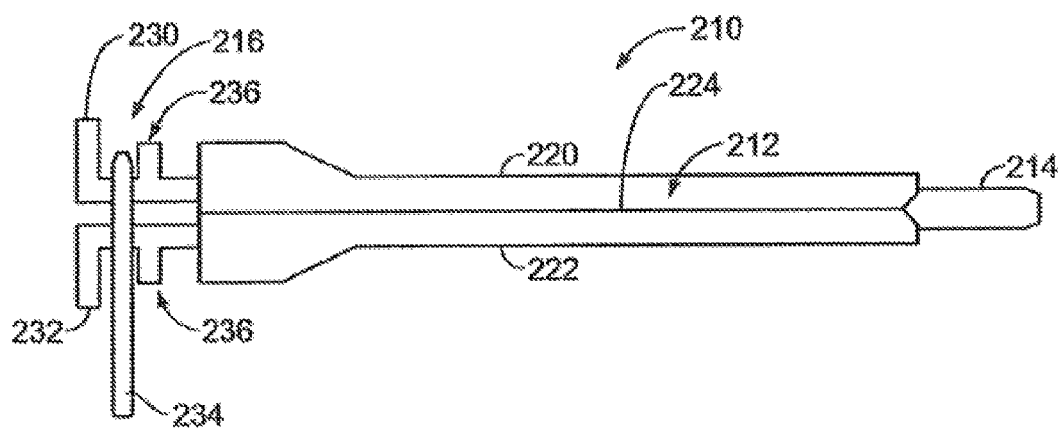
FIG. 16 illustrates an overhead view of a spinal implant system including a funnel, a spacer, and a double-barreled plunger formed in accordance with an embodiment of the present invention.
Figure 17:
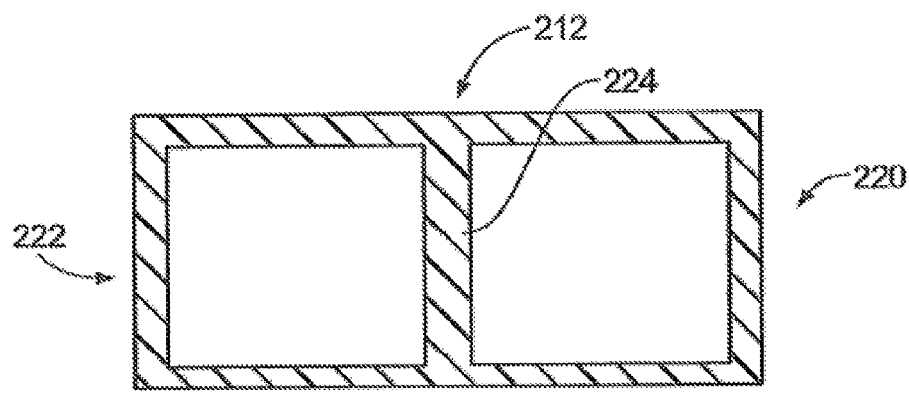
FIG. 17 illustrates a sectional view through the funnel of FIG. 16.

FIG. 16 illustrates an overhead view of a spinal implant system 210 including a funnel 212, a spacer 214, and a double-barreled plunger 216, and FIG. 17 illustrates a sectional view of the funnel 212. While the spinal implant system 210 is similar in many respects to the above described embodiments, the spinal implant system 210 further allows choosing between simultaneous and independent delivery of bone graft material to either side of the spacer 214.

The funnel 212 includes a length that is generally rectangular, and includes a first portion 220 and a second portion 222 separated by a wall 224 that runs along the length of the funnel 212. In alternate embodiments, the wall may not run along the entire length of the funnel. In the illustrated embodiment, the funnel 212 is substantially rectangular, with a width greater than its height. In alternate embodiments, different shapes may be used, such as, for example, generally oval. The funnel 212 is sized to provide a desired amount of bone graft material to either side of the spacer 214, while still maintaining a desired size to reduce the invasiveness of its use.

The double-barreled plunger 216 includes a first plunger 230, a second plunger 232, and a handle 234. The first plunger 230 and second plunger 232 are generally similar, and configured to be accepted by a portion of the funnel 212 to advance bone graft material down that half of the funnel 212. Each plunger 230, 232 includes a grasping portion 236 proximate to its proximal end. In the illustrated embodiment, the grasping portion 236 is configured to perform two functions. First, the grasping portion 236 may be handled by a practitioner to advance one plunger 230, 232 at a time through the funnel 212, thereby advancing bone graft material only along one half of the funnel and to only one side of the spacer 214, or allowing the plungers 230, 232 to be advanced independently of each other at different rates and/or for different lengths of advancement. Second, the grasping portions 236 may be joined to the handle 234 to advance both plungers 230, 232 simultaneously. The handle 234 includes features that cooperate with features of the grasping portions 236 to join the first and second plungers 230, 232 to the handle 234. For example, the handle 234 may include slots that accept portions of the grasping portions 236. Thus, the spinal implant system 210 allows for either independent or simultaneous distribution of bone graft material to either side of the spacer 214, thereby allowing greater control of the volume and location of bone graft material distributed.

For example, both portions of the funnel 212 may be filled with bone graft material, both plungers depressed, and a generally equal amount of bone graft material distributed to each side of the spacer 214. However, if one side requires more bone graft material than first distributed, but the other side does not, then additional bone graft material may be added only to the desired portion of the plunger. As another example, if the plungers are initially depressed, and it is discovered that along the length of their travel that one, but only side, has all the bone graft material desired, then the handle 234 may be decoupled from the plungers 230, 232, and only the plunger on the side still requiring bone graft material may be advanced.

Figure 18:
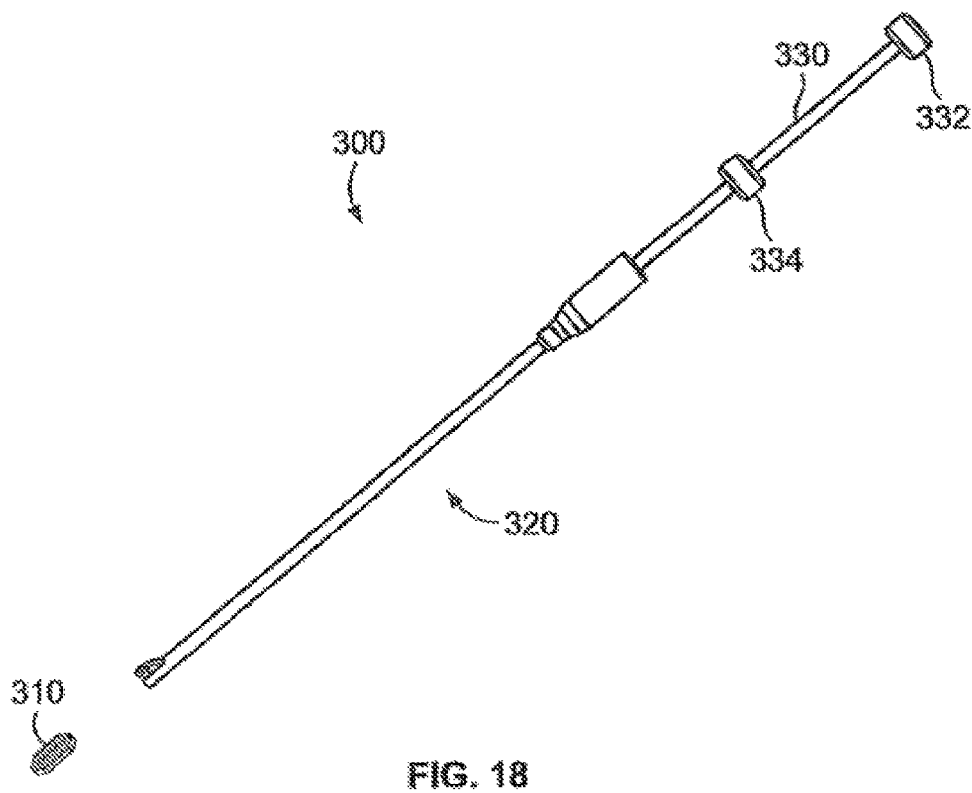
FIG. 18 illustrates a perspective view of a spinal implant system including a funnel, a spacer, and a tamping rod.

FIG. 18 illustrates a perspective view of a spinal implant system 300 formed in accordance with an embodiment of the present invention. The spinal implant system includes a spacer 310, a funnel 320, and a tamping rod 330. The spacer 310 may be similar in many respects to the spacers discussed above. The illustrated funnel 320 is asymmetric, similar to funnel 172, for example. Funnel 320, however, is generally circular in cross-section along most of its length. Further, the funnel 320, toward its proximal end, includes a mouth having a larger diameter to ease insertion of bone graft material. The tamping rod 330 is a type of plunger. The tamping rod 330 includes a handle 332 and a stop 334. The handle 332 is a generally circular shaped feature, located at the proximal end of the tamping rod 330, and configured to provide a convenient location for grasping of the tamping rod 330 by a practitioner. The stop 334 is a generally circularly shaped feature, located at a length along the tamping rod 330 to prevent the tamping rod 330 from being urged too far down the funnel 320, where the tamping rod could otherwise potentially disturb aspects of a patient's anatomy and/or the placement of the spacer 310 between the patient's vertebrae. In the illustrated embodiment, the stop 334 has a diameter sufficient large to prevent it from advancing beyond the proximal edge of the enlarged bell mouth of the funnel 320.

To use a spinal implant system in accordance with an embodiment of the present invention, the following steps may be performed. First, an incision is made to access the site of interest. Next, a pocket for placement of a spacer is prepared, for example, by scraping surfaces of the vertebrae to be fixed. Next, the correct size of spacer is selected. The spacer may be joined to an inserter, and advanced to the site of interest in its horizontal orientation. Then, the inserter (and spacer with it) is rotated to position the vertebrae as desired. The inserter is then removed and a funnel positioned. For example, if during the creation of the pocket the practitioner observes that one side is likely to require a different volume of bone graft material than the other, an asymmetric funnel may be selected, or alternatively, a plunger with a double-barreled funnel selected. The bone graft material is then added as desired.

In certain embodiments of the present invention, a kit is provided including a variety of sizes and/or types of funnels, and/or a variety of sizes and/or types of inserters, and/or a variety of sizes and/or types of spacers to accommodate different patients and procedures.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A spacer for maintaining the position of adjacent vertebrae, the spacer including:
   a distal end and a proximal end;
   top and bottom surfaces spaced by at least two sides, the top and bottom surfaces defining a height, and the sides defining a width;
   wherein each of the two sides comprises a depressed region sunk into the side including a sloped surface at least toward the proximal end of the spacer, the distance between the sloped surfaces of the sides decreasing proximally to form a web, and
   wherein the web is sized and configured to aid distribution of bone graft material to either side of the spacer, wherein the web separates a top cap and a bottom cap at least at the proximal end of the spacer, the thickness of the web decreasing proximally to form a wedge, and wherein the top cap and the bottom cap include surfaces that taper such that the top cap and bottom cap become narrower toward the proximal end of the spacer.

2. The spacer of claim 1, wherein the wedge includes a tip defining a generally sharp point.

3. The spacer of claim 1, wherein the sloped surfaces are sloped generally continuously along their length.

4. The spacer of claim 1, wherein the depressed regions each include first and second surfaces, the first and second surfaces being sloped differently.

5. The spacer of claim 1 wherein at least one of the depressed regions includes a mounting feature configured to help secure the spacer with at least one of an inserter and a funnel.

6. The spacer of claim 1 wherein the height is greater than the width, wherein the spacer may be inserted with the sides oriented toward surfaces of adjacent vertebrae, and then rotated into place with the top and bottom surfaces oriented toward the surfaces of the adjacent vertebrae to maintain a space between the adjacent vertebrae.

7. A system for positioning and fixing an implant between adjacent vertebrae, the system including:
   a spacer including
      a distal end and a proximal end;
      top and bottom surfaces spaced by at least two sides, the top and bottom surfaces defining a height, and the sides defining a width;
      wherein each of the two sides comprises a depressed region sunk into the side including a sloped surface at least toward the proximal end of the spacer, the distance between the sloped surfaces of the sides decreasing proximally to form a web, and wherein the web is sized and configured to aid distribution of bone graft material to either side of the spacer;
   a feed reservoir defining a passageway through which bone graft material may be delivered to the spacer when the spacer is positioned as desired between adjacent vertebrae, the feed reservoir including an alignment feature configured to align the feed reservoir with the spacer so that bone graft material delivered to the spacer through the feed reservoir is distributed to at least one side of the web of the spacer; and
   a plunger configured to be accepted by the passageway of the feed reservoir, the plunger configured to help advance bone graft material along a length of the feed reservoir.

8. The system of claim 7 wherein the web separates a top cap and a bottom cap at least at the proximal end of the spacer, the thickness of the web decreasing proximally to form a wedge.

9. The system of claim 8 wherein the alignment feature of the feed reservoir includes a notch sized to be accepted by the web.

10. The system of claim 8 wherein the top cap and the bottom cap include surfaces that taper such that the top cap and bottom cap become narrower toward the proximal end of the spacer.

11. The system of claim 10 wherein the alignment feature of the feed reservoir includes a notch cut through top and bottom walls of the feed reservoir, the notch sized and configured to accept a portion of the top cap and bottom cap of the spacer.

12. The system of claim 7 wherein the feed reservoir is asymmetric about a vertical plane through the center of the spacer when the feed reservoir is aligned with the spacer.

13. The system of claim 7 further comprising an inserter, wherein the inserter includes the feed reservoir and a gripping portion, the gripping portion configured to grasp the spacer during insertion and positioning of the spacer.

14. The system of claim 13 wherein the height of the spacer is greater than the width, wherein the spacer may be inserted with the sides oriented toward surfaces of adjacent vertebrae, and then rotated into place with the top and bottom surfaces oriented toward the surfaces of the adjacent vertebrae to maintain a space between the adjacent vertebrae, and wherein the gripping portion of the inserter includes a load bearing portion sized to contact vertebrae during rotation of the spacer.

15. The system of claim 13 wherein the gripping portion includes a graft opening sized and configured to allow bone graft material to be distributed to at least one side of the spacer when the spacer is positioned in the gripping portion.

16. The system of claim 7 wherein the feed reservoir includes a first portion and a second portion separated by a wall, and the plunger includes a first plunger and a second plunger, the first plunger accepted by the first portion of the feed reservoir and the second plunger accepted by the second portion of the feed reservoir, wherein bone graft material can be advanced down the portions of the feed reservoir either independently or simultaneously.

17. The system of claim 16 wherein the plunger includes a handle and the first plunger and the second plunger are removably joined to the handle.

18. The system of claim 7 wherein the height of the spacer is greater than the width, wherein the spacer may be inserted with the sides oriented toward surfaces of adjacent vertebrae, and then rotated into place with the top and bottom surfaces oriented toward the surfaces of the adjacent vertebrae to maintain a space between the adjacent vertebrae.

19. A method of maintaining adjacent vertebrae in a desired position, the method including:
   providing a spacer having
      a distal end and a proximal end;
      top and bottom surfaces spaced by at least two sides, the top and bottom surfaces defining a height, and the sides defining a width;
      wherein each of the two sides comprises a depressed region sunk into the side including a sloped surface at least toward the proximal end of the spacer, the distance between the sloped surfaces of the sides decreasing proximally to form a web, and wherein the web is sized and configured to aid distribution of bone graft material to either side of the spacer;

positioning the spacer between the adjacent vertebrae;
positioning a feed reservoir so that a passageway of the feed reservoir is proximate to the wedge of the spacer;
introducing bone graft material through the feed reservoir to a site of interest proximate to the spacer, wherein the bone graft material is directed by the web to be distributed to a site proximate to at least one side of the spacer.

20. The method of claim 19 wherein the height of the spacer is greater than the width, wherein the spacer may be inserted with the sides oriented toward surfaces of adjacent vertebrae, and then rotated into place with the top and bottom surfaces oriented toward the surfaces of the adjacent vertebrae to maintain a space between the adjacent vertebrae, and wherein positioning the spacer includes positioning the spacer between the adjacent vertebrae with the sides oriented toward surfaces of adjacent vertebrae, the method further including the step of rotating the spacer so that the top and bottom surfaces are oriented toward the surfaces of the adjacent vertebrae to maintain a desired space between the adjacent vertebrae after positioning the spacer between the adjacent vertebrae with the sides oriented toward surfaces of adjacent vertebrae.

* * * * *